US005763393A

United States Patent [19]
Moskal et al.

[11] Patent Number: 5,763,393
[45] Date of Patent: Jun. 9, 1998

[54] NEUROACTIVE PEPTIDES

[75] Inventors: Joseph R. Moskal, Chicago; Hirotaka Yamamoto, Glenview; Patricia A. Colley, Chicago, all of Ill.

[73] Assignee: Neurotherapeutics L.P., Chicago, Ill.

[21] Appl. No.: 649,272

[22] Filed: May 17, 1996

[51] Int. Cl.$^6$ ................................................ A61K 38/00
[52] U.S. Cl. ........................ 514/2; 530/300; 530/328; 530/326
[58] Field of Search ................................ 530/326, 300, 530/328; 514/2

[56] References Cited

PUBLICATIONS

Akase et al. (1994) "A system for quantitative analysis of associative learning" J. Neurosci. Meth. 54:119–130.

Bekenstein et al. (1990) "Autoradiographic evidence that NMDA receptor–coupled channels are located postsynaptically and not presynaptically in the preforant path–dentate granule cell system of the rat hippocampal formation" Brain Research 514(2):334–342.

Bliss et al. (1993) "A synaptic model of memory: long–term potentiation in the hippocampus" Nature 361:31–39.

Brandeis et al. (1989) "The use of the Morris water maze in the study of memory and learning" Int. J. Neurosci. 48:29–69.

Disterhoft et al. (1977) "Nictitating membrane conditioning to tone in the immobilized albino rabbit" Brain Res. 137:127–143.

Haring et al. (1991) "Glycine–like modulation of N–methyl–D–aspartate receptors by a monoclonal antibody that enhances long–term potentiation" J. Neurochem: 1–10.

Hofman (1991) "NMDA receptor cloned—Twice?" Science 254:801–802.

Kelso et al. (1992) "Protein Kinase C—mediated enhancement of NMDA currents by metabotropic glutamate receptors in xenopus oocytes" J. of Physiology 449:705–718.

Kozikowski et al. (1990) "Synthesis and bioactivity of a new class of rigid glutamate analogues. Modulators of the N–Methyl–D–aspartate receptor" J of Med. Chem. 33:1561–1571.

Leonard & Kelso (1990) "Apparent desensitization of NMDA responses in Xenopus Oocytes involves calcium–dependent chloride current" Neuron 4:53–60.

Morris (1984) "Developments of a water–maze procedure for studying spatial learning in the rat" J. Neurosci. Methods 11:47–60.

Moskal et al. (1986) "Monoclonal antibodies to the dendrate gyrus: immunocytochemical characterization and flow cytometric analysis of hippocampal neurons bearing a unique cell–surface antigen" J. Neurosci. 6(7):2045–2053.

Moyer et al. (1990) "Hippocampectomy disrupts trace eye–blink conditioning in rabbits" Behav. Neurosci. 104:243–252.

Opello et al. (1993) "AF64A impairs acquisition and performance of a spatial, but not a cued water maze task: relation to cholinergic hypofunction" Physiology & Behaviour 54(6):1227–1233.

Skelton (1988) "Bilateral cerebellar lesions disrupt conditioned eyelid responses in unrestrained rats" Behav. Neurosci. 102(4):586–590.

Stanton et al. (1987) Inhibition of the production and maintenance of long–term potentiation in rat hippocampal slices by a monoclonal antibody: PNAS(USA) 84(6):1684–1688.

Thompson et al. (1992) "Hippocampus–dependent learning facilitated by a monoclonal antibody of d–Cycloserine" Nature 359:638–641.

Thompson et al. (1994) "A system for quantitative analysis of associative learning. Part 1. Hardware interfaces with cross–species applications" J. Neurosci. Meth. 54:109–117.

Tonkiss & Rawlins (1991) "The competitive NMDA antagonist AP5, but not the non–competitive antagonist MK801, induces delay–related impairment in spatial working memory in rats" Exp. Brain Res. 85:349–358.

Weiss & Thompson (1992) "Delayed acquisition of eyeblink conditioning in aged F1 hybrid (Fischer–344) x brown Norway) rat" Neurobiol. Aging 13:319–323.

Loman, K.L. et al. 1991 Gene 105:283–284.
Kelley, D.E. et al. 1982 Cell 29:681–689.
Rabbitts, T.H. et al. 1980 Can. J. Biochem. 58:176–189.
Shimizu, T. et al. 1991 J. Exp. Med. 173:1065–1072.

*Primary Examiner*—Lila Feisee
*Assistant Examiner*—Minh-Tam Davis
*Attorney, Agent, or Firm*—McDonnell Bohnen Hulbert & Berghoff

[57] ABSTRACT

Compositions and methods are described for the specific identification of NMDA receptors, and for the specific identification and manipulation of NMDA glycine co-agonist biological activity.

6 Claims, 6 Drawing Sheets

NEUROACTIVE PEPTIDES

BACKGROUND OF THE INVENTION

1. Field of the Invention

The instant invention is related to the field of neuroactive peptides, proteins, or amino acid compositions.

2. Description of the Related Art

It is now well known that the central nervous system (CNS) of mammals employs many neuroactive peptides to effect specialized signalling within the brain and spinal cord. Among the more well known neuroactive peptides are Somatostatin, Cholecystokinin, VIP, Substance P, Enkephalin, Neuropeptide Y (NPY), Neurotensin, TRH, CCK, and dynorphin. (see generally *The Biochemical Basis of Neuropharmacology*, Cooper, Bloom and Roth, 5th ed., Oxford University Press, New York, 1986). The careful elucidation of the complex signalling pathways which operate in the CNS requires the identification and characterization of specific neuroactive peptides and their particular properties, as well as the characterization and localization of specific neurologically significant receptors. Identification of agonists and antagonists of CNS receptors, whether partial, complete, coordinately acting, or independently acting, is useful in that the more that is known of specific neuroactive peptides, the greater the range of manipulations that can be conducted on CNS receptor proteins, and the behavior of CNS receptor complexes. Significantly, the identification of unique agonists or antagonists allows for the fine characterization and localization of subsets of neuroactive receptors by their binding to these agonists or antagonists. By identifying neuroactive peptides, and using them to specifically perturb the behavior of known receptor complexes, more detailed understanding becomes available about the receptor complex. In addition, new neuroactive peptides offer alternative means of altering the behavior of known CNS receptor complexes, or for the discovery of previously unknown receptor complexes or unknown behavior of known receptors.

The N-methyl-D-aspartate (NMDA) receptor, which has been implicated in neurodegenerative disorders, stroke-related brain cell death, convulsive disorders, and learning and memory, has been cloned from human tissue (see Hoffman, M., 1991, *Science*, 254:801–2). In addition to being activated by the binding of NMDA, the NMDA receptors are activated by glutamate (Glu), and aspartate (Asp), as well as being competitively antagonized by D-2-amino-5-phosphonovalerate (D-AP5; D-APV), or non-competitively antagonized by phenylcyclidine (PCP), and MK-801. However, most interestingly, the NMDA receptor is coactivated by glycine (Gly). (Kozikowski et al., 1990, *Journal of Medicinal Chemistry* 33:1561–1571). The binding of glycine to an allosteric regulatory site on the NMDA receptor complex increases both the duration of channel open time, and most dramatically the frequency of the opening of the NMDA receptor channel.

The NMDA receptor is considered central to long-term potentiation (LTP), which is the persistent strengthening of neuronal connections that is considered to underlie learning and memory (see Bliss and Collingridge, 1993, *Nature* 361:31–39, for review). Damage to the CNS, which may occur for example during a stroke, is thought to be caused by the overexcitement of cells which have the NMDA receptor, by flooding these cells with glutamate or aspartate, leading to the death of some 80% of such overexcited cells. The bulk of NMDA receptor-carrying cells are in the cortex and hippocampus regions of the brain, and after such overexcited killing of cells, patients are rendered incapable of learning new things, but can still recall items in long term memory. Human memory deficits associated with PCP abuse have been linked to the action of PCP, and is an expected consequence of the inhibition of calcium fluxes through the NMDA receptor.

It is thought that drugs which can block, or otherwise alter the operation of the NMDA receptor may protect cells from overexcited killing, or NMDA receptor associated memory problems. Other drugs that interact with the NMDA receptor may enhance the ability of the cells to form LTP and thus enhance learning and memory.

Because of the significance of the NMDA receptor, it would be most useful to have specific peptide agonists or antagonists which will allow for fine mapping of the tissue distribution, subtype characterization, and fine manipulation of NMDA receptors, and for characterization of the action of other agonists or antagonists on the NMDA receptor.

SUMMARY OF THE INVENTION

The instant invention provides certain specific neuroactive peptides which are characterized by the ability to bind to the NMDA receptor. The instant invention provides for specific polypeptides or amino acid compositions which bind to the NMDA receptor at the glycine co-agonist site, and effect at least the same biological activity from the NNDA receptor as the binding of glycine. Polypeptides or amino acid compositions of the instant invention may be purified from natural tissues, fluids, or cells. A preferred embodiment of the instant invention provides for the chemical synthesis of the polypeptides or amino acid compositions of the instant invention using conventional biochemistry methods, or molecular biology techniques. As the polypeptides or amino acid compositions of the instant invention are useful for the isolation and characterization of NMDA receptor activity and tissue localization, the instant invention provides for stabilized polypeptides or amino acid compositions wherein the backbone has incorporated modified peptides such that stability is enhanced, or via addition of framework modifications such that the three-dimensional conformation of the peptide fragment is stabilized or enhanced. The instant invention also provides for cyclized polypeptides or amino acid compositions.

An additional benefit of the polypeptides or amino acid compositions of the instant invention is that the small size will enhance the ability to cross the blood-brain barrier, and are thus suitable for in vivo administration and detection. Thus the instant invention encompasses polypeptides or amino acid compositions of the instant invention coupled to radioactive markers, MRI markers, metal ion markers, enzymatic markers, chemiluminescent markers, or any such marker which will allow for the detection of the polypeptide or amino acid compositions. The instant invention also encompasses pharmaceutical formulations of the polypeptides or amino acid compositions of the instant invention, in suitable pharmaceutical carriers such that they can be administered to a living subject. Such administration can be i.p., i.v., i.m., or by any other appropriate means.

In instances where the polypeptides or amino acid compositions of the instant invention are used for detection of NMDA receptors using in vitro screening such as tissue section and staining, the attached marker can also be, in addition to the suitable markers above, proteins, antibody, avidin, biotin, and any other such marker which allows for the detection of the presence of polypeptide or amino acid compositions in screening assays or staining procedures.

The instant invention also provides for methods of detecting NMDA receptors using the polypeptides or amino acid compositions of the instant invention and an appropriate marker for detection of the bound receptor and polypeptide or amino acid composition. Such methods can be practiced in vitro and in vivo depending on the conditions for detection used. Certain procedures which can be employed using such methods include, and are not limited to, MRI, CAT scan, X-ray, Sonogram, and other such non-invasive detection methodologies. Where invasive procedures are contemplated, ie. biopsy or tissue section, the use of standard immunological screening methods can be used to detect the presence of bound receptor/polypeptide, or such binding can be specifically visualized via immunological staining or other such detection means utilizing the wide range of available marker/detection systems. The instant invention therefore also provides for a method for modifying the biological activity of a NMDA receptor comprising said NMDA receptor contacting with a polypeptide or amino acid composition of the instant invention. Specifically encompassed are peptides having the amino acid sequences as listed in Table 1 below, that are predicted to be effective by assay data in the following examples.

expression system, an electrophysiological NMDA-specific function assay.

FIG. 3A shows the dose-dependent effects of NT-13 on NMDA currents by voltage-clamp experiments. FIGS. 3B–D demonstrate that peptide NT-13 has characteristics of a partial glycine agonist.

FIG. 3B shows that NT-13 mimics glycine, but is not as effective.

FIG. 3C shows that NT-13 inhibits the standard NMDA+ glycine current.

FIG. 3D shows that the NT-13-induced NMDA current is blocked by 7-chlorokynurenic acid, which is a selective glycine site antagonist.

FIG. 4 shows the results of testing peptide NT-13 as a partial agonist in a behavioral NMDA-specific function assay compared with cerebral spinal fluid control (CSF) and mAb B6B21. FIG. 4 shows that peptide NT-13 produced some cognitive enhancement in the Morris water maze task as measured by short latencies to swim to the submerged platform (FIG. 4A), path lengths to the platform (FIG. 4B), and decreased average distance to the target during the probe trial on Day 8 of training (FIG. 4C).

TABLE 1

| Name SEQ ID NO | Amino Acid Sequence |
|---|---|
| NT-1: SEQ ID. NO:1. | Lys—Ala—Ser—Gln—Asp—Val—Ser—Thr—Thr—Val—Ala |
| NT-2: SEQ ID. NO:2. | Ser—Ala—Ser—Tyr—Arg—Tyr—Thr |
| NT-3: SEQ ID. NO:3. | Gln—Gln—His—Tyr—Ser—Thr—Pro—Pro—Thr |
| NT-4: SEQ ID. NO:4. | Val—Tyr—Tyr—Ser—Gln—Gln—His—Tyr—Ser—Thr—Pro—Pro—Thr |
| NT-5: SEQ ID. NO:5. | Glu—Asp—Leu—Ala—Val—Tyr—Tyr—Ser—Gln—Gln—His—Tyr—Ser—Thr—Pro—Pro—Thr |
| NT-6: SEQ ID. NO:6. | Ser—Val—Gln—Ala—Glu—Leu—Asp—Leu—Ala—Val—Tyr—Tyr—Ser—Gln—Gln—His—Tyr—Ser—Thr—Pro—Pro—Thr |
| NT-7: SEQ ID. NO:7. | Phe—Thr—Ile—Ser—Ser—Val—Gln—Ala—Glu—Leu—Asp—Leu—Ala—Val—Tyr—Tyr—Ser—Gln—Gln—His—Tyr—Ser—Thr—Pro—Pro—Thr |
| NT-8: SEQ ID. NO: 8. | Gln—Gln—His—Tyr—Ser—Thr—Pro—Pro—Thr—Phe—Gly—Gly—Gly |
| NT-9: SEQ ID. NO:9. | Gln—Gln—His—Tyr—Ser—Thr—Pro—Pro—Thr—Phe—Gly—Gly—Gly—Thr—Lys—Leu—Glu |
| NT-10: SEQ ID. NO:10 | Cys—Gln—Gln—His—Tyr—Ser—Thr—Pro—Pro—Thr—Cys (S—S disulfide bond) |
| NT-11: SEQ ID. NO:11 | Ser—Gln—Gln—His—Tyr—Ser—Thr—Pro—Pro—Thr—Ser |
| NT-12: SEQ ID. NO:12 | Gln—Gln—His—Tyr—Ser |
| NT-13: SEQ ID. NO:13 | Thr—Pro—Pro—Thr |
| NT-14: SEQ ID. NO:14 | Thr—Pro—Pro |
| NT-15: SEQ ID. NO:15 | Pro—Pro—Thr |
| NT-16: SEQ ID. NO:16 | Pro—Pro |
| NT-17: SEQ ID. NO:17 | Thr—Pro—Thr |
| NT-18: SEQ ID. NO:18 | Thr |

DETAILED DESCRIPTION OF THE INVENTION

EXAMPLE 1

Monoclonal Antibody specific for NMDA receptors

Figure 1A:
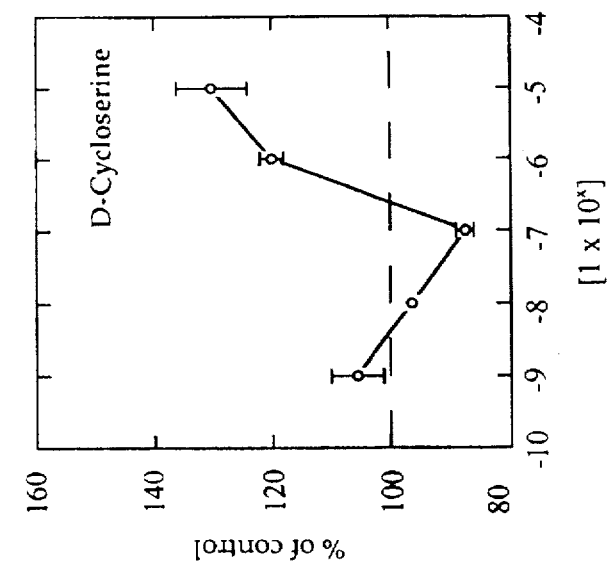
FIG. 1A shows activity of D-cycloserine, 1B shows the activity of monoclonal antibody B6B21, and 1C shows the activity of peptide NT-3. Results are plotted as concentration of test component v. percentage of control binding of [³H]MK-801 in the presence of 7-chlorokynurenic acid, a selective glycine site agonist.

Monoclonal antibodies were generated by immunizing mice with dentate gyrus tissue isolated from 5 day old neonatal rats following standard protocols (see Moskal and Schaffner, 1986, *The Journal of Neuroscience*, 6(7)

:2045–2053). After screening the hybridomas for binding to dentate gyrus tissue via histochemical methods, promising candidate clones were isolated. Among the isolated clones was monoclonal antibody B6E11 which was found to block the production of LTP in rat hippocampal slices, and to suppress established LTP in both area CA1 of the hippocampus and the dentate gyrus (see Stanton, Sarvey and Moskal, 1987, *Proceedings of the National Acadamy of Science, U.S.A.*, 84:1684–1688). The monoclonal antibody B6E11 was found to be effective in blocking LTP when applied to the apical dendrites synapsing with the potentiating input, but not when applied to cell bodies or to the basal dendrites of CA1. In contrast, a second monoclonal antibody, G6E3, which was from the same panel, of the same immunoglobulin class, and bound to the target tissue in a similar fashion, did not have any effect on LTP.

Another monoclonal antibody, B6B21, was found to enhance LTP by glycine-like modulation of the NMDA receptor (see Haring, Stanton, Scheideler and Moskal, 1991, *Journal of Neurochemistry*, 57(1):323–332). This unique monoclonal antibody was able to significantly elevate LTP when applied to CA1 pyramidal cell apical dendrites in rat hippocampal slices. B6B21 also elevated binding of N-(-1-(2-thienyl)cyclohexyl)-3,4-[$^3$H]piperdine ([$^3$H]-TCP) to the intra-channel PCP site. This effect was eliminated by the maximal saturation of the NMDA receptors with combined addition of maximal concentrations of glutamate, glycine, and magnesium. Most importantly, monoclonal antibody B6B21 reversed 7-chlorokynurenic acid inhibition of [$^3$H]-TCP binding, but had no effect on the inhibition of [$^3$H]-TCP binding by APV. The enhancement of the binding of [$^3$H]-TCP by monoclonal antibody B6B21 was increased by glutamate but not glycine.

Hippocampus-dependent learning was found to be facilitated by the binding of B6B21, or the addition of D-cycloserine, both of which bind specifically to the NMDA receptor, in in vivo experiments utilizing a rabbit eyeblink conditioning test (see Thompson, Moskal and Disterhoft, 1992, Nature, 359:638–641). Intraventricular (into the brain ventricle) infusions of B6B21 significantly enhanced acquisition rates in hippocampus-dependent trace eyeblink conditioning in rabbits, halving the number of trials required to reach a criterion of 80% conditioned responses. Peripherial injections of D-cycloserine, a partial agonist of the glycine site on the NMDA receptor which crosses the blood-brain barrier, also doubled the rabbits' learning rates.

Study of the monoclonal antibody B6B21 allowed us to generate a panel of polypeptides or amino acid compositions (Table 1) which allow for the mimicking of the activity of the mAb B6B21, and thus the glycine co-agonist effect.

EXAMPLE 2

Pharmacological NMDA Specific Activity—[$^3$H] MK-801 Assay

The peptides of the instant invention are capable of specific binding to the mammalian NMDA receptor at the glycine co-agonist site. Remarkably, the peptides of the instant invention do not require the presence of a glycine (Gly, G) amino acid. Because of the significant role the NMDA receptor plays in the mammalian brain, specific agonists are very useful for the fine mapping of NMDA receptor tissue distribution, and correlation with disease, injury, or other pharmacological effects. Specific small peptide agonists are particularly useful in that they can be further modified for enhanced bioavailabilty and for transport across the blood-brain barrier.

Polypeptides or amino acid compositions of the instant invention were tested for the ability to mimic the glycine co-agonist effect on the NMDA receptor using a previously validated [$^3$H]MK-801 binding assay. This functional assay takes advantage of the fact that increased [$^3$H]MK-801 binding by NMDA receptors can only occur upon receptor-binding channel opening. This is because the MK-801 binding site is located inside the ionophore of the NMDA receptor complex, and is thus only accessible upon the opening of the receptor-channel complex. Thus increased binding of [$^3$H]MK-801 is directly correlated with increased channel opening, in this assay, triggered by the binding of the polypeptides or amino acid compositions of the instant invention to the glycine co-agonist binding site.

To further refine the assay, a selective antagonist of the glycine binding site of the NMDA receptor-channel complex is added to the assay. The normal action of 7-chlorokynurenic acid is to selectively bind to the glycine site, and inhibit NMDA receptor channel opening, and thus inhibit the binding of [$^3$H]MK-801 to the NMDA receptor complex. The addition of peptide NT-13 reversed the inhibition of binding of [$^3$H]MK-801, and thus correlates with the finding that the polypeptides or amino acid compositions of the instant invention bind to the glycine binding site.

Membrane Preparation

Crude synaptic membranes used in the assay were prepared using rat hippocampal tissue (male Sprague-Dawly rats) and extensively washed using the procedures described previously (Haring et al., 1991, *J. Neurochem.* 57:323–331). Briefly, tissue which has been stored at −80° C. is homogenized in ice cold 5 mM Tris (pH 7.4) using a Brinkman Polytron® and then pelleted by centrifugation at 48,000 g for 20 minutes. The resulting supernatant is discarded, and the membranes washed three times in cold buffer. Pellets are then resuspended in 5 mM EDTA, 15 mM Tris (pH 7.4), and incubated for one hour at 37° C. The membrane suspensions are then pelleted by centrifugation at 48,000 g for 20 min and stored at −80° C. until use in the assay.

Receptor Binding Assay

Frozen pellets are thawed at room temperature and washed three times by resuspension in 5 mM Tris (pH 7.4) and centrifugation. Final pellets are suspended at concentrations of 2 to 3 mg/ml in 5 mM Tris buffer (pH 7.4). Binding reactions are initiated by the addition of 200 μg of freshly prepared membranes to reaction mixtures (about 1 ml final volume) containing 1 nM [$^3$H]MK-801 at 25° C. in the presence of a range of peptide concentrations and 60 μM 7-chlorokynurenic acid. Non-specific binding is determined using 10 μM unlabelled MK-801. Binding reactions are terminated by filtration through a Brandel 24-well cell harvester onto Whatman GF/B glass filters that have been presoaked in 0.25% polyethyleneimine for 30 minutes.

Data Analysis/Interpretation

Peptides which stimulate [$^3$H]MK-801 binding at concentrations equal to or less than the effective dose of D-cycloserine (at $10^{-5}$) are deemed to be positive for ability to bind the glycine site of the NMDA receptor complex.

Figure 1B:
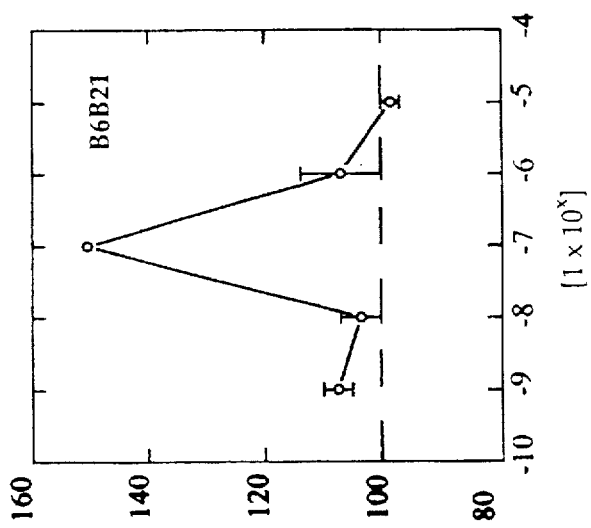
FIG. 1 shows three graphs comparing results of testing for NMDA receptor binding glycine agonists using a pharmacological NMDA-specific function [³H]MK-801 binding assay.
Figure 1C:
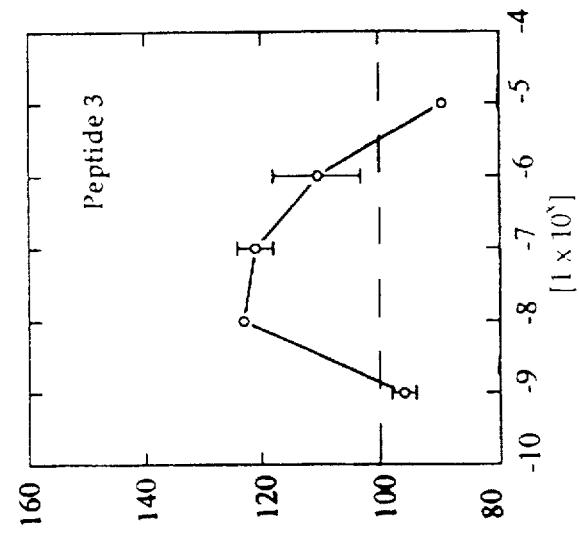

FIG. 1 shows data comparing the binding data using D-cycloserine (FIG. 1A), mAb B6B21 (FIG. 1B), and peptide NT-3 (FIG. 1C). FIG. 1C clearly shows that peptide NT-3 binds to the glycine site of the NMDA receptor in a fashion similar to mAb B6B21 and D-cycloserine. Data is reported as % control binding in the presence of 7-chlorokynurenic acid against concentration of tested material.

Figure 2:
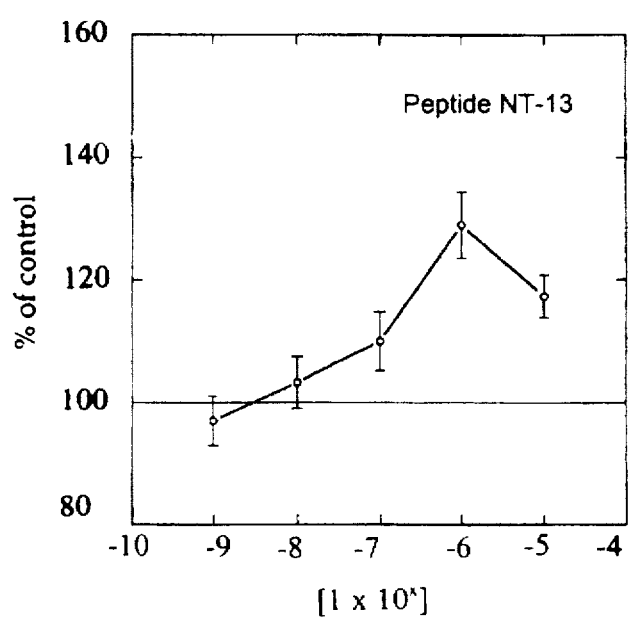
FIG. 2 shows the results of testing peptide NT-13 as a partial agonist in a pharmacological NMDA-specific function assay as measured by the [³H]MK-801 binding.

FIG. 2 shows the binding activity of peptide NT-13 as above. Data is reported as % control binding in the presence of 7-chlorokynurenic acid against concentration of tested material.

Table 2 below lists results from assay results using the peptides of the instant invention.

TABLE 2

|       | $10^{-9}$M | $10^{-8}$M | $10^{-7}$M | $10^{-6}$M | $10^{-5}$M |
|-------|------------|------------|------------|------------|------------|
| NT-1* |            |            | 97 ± 2     | 100 ± 2    | 73 ± 6     |
| NT-2* |            | 80 ± 9     | 109 ± 15   | 106 ± 4    | 77 ± 12    |
| NT-3  | 112 ± 20   | 123 ± 0    | 121 ± 4    | 111 ± 11   | 90 ± 1     |
| NT-4  | 106 ± 2    | 106 ± 6    | 116 ± 2    | 110 ± 1    | 109 ± 10   |
| NT-5  | 109 ± 8    | 100 ± 9    | 114 ± 2    | 106 ± 2    | 112 ± 4    |
| NT-6  | 95 ± 6     | 101 ± 9    | 101 ± 15   | 96 ± 1     | 91 ± 7     |
| NT-7  | 96 ± 4     | 103 ± 4    | 97 ± 1     | 104 ± 0    | 100 ± 3    |
| NT-8  | 105 ± 7    | 110 ± 5    | 108 ± 4    | 107 ± 6    | 115 ± 6    |
| NT-9  | 104 ± 12   | 126 ± 7    | 125 ± 5    | 112 ± 10   | 120 ± 3    |
| NT-10 | 100 ± 2    | 90 ± 8     | 114 ± 3    | 128 ± 4    | 116 ± 12   |
| NT-11 | 96 ± 23    | 111 ± 4    | 118 ± 4    | 120 ± 11   | 127 ± 21   |
| NT-12 | 95 ± 21    | 104 ± 10   | 95 ± 7     | 106 ± 9    | 106 ± 2    |
| NT-13 | 97 ± 8     | 103 ± 8    | 110 ± 10   | 129 ± 10   | 117 ± 7    |
| NT-14 | 89 ± 6     | 101 ± 1    | 96 ± 5     | 98 ± 8     | 95 ± 4     |
| NT-15 | 99 ± 21    | 103 ± 2    | 100 ± 7    | 108 ± 12   | 93 ± 1     |
| NT-16 | 83 ± 9     | 89 ± 8     | 97 ± 6     | 103 ± 3    | 117 ± 12   |
| NT-17 | 122 ± 23   | 125 ± 17   | 128 ± 9    | 117 ± 14   | 119 ± 21   |
| NT-18 | 88 ± 21    | 104 ± 33   | 101 ± 4    | 103 ± 6    | 123 ± 19   |

*In the presence of 10 µM L-glutamate

Table 2 shows the effect of peptides NT-1 through NT-18 on NMDA receptor activation as measured by [$^3$H]MK-801 binding in rat hippocampus, reported as a percentage of control binding (±S.E.M.) at various concentrations of peptide. The data reported for peptides NT-15 through NT-18 and the experimental error for each point make it unlikely that any of these peptides have meaningful biological activity. It should be emphasized that peptide concentrations of $10^{-5}$M, approaching millimolar range (100 mM), for efficacious concentration are too high to be considered reliable indicators that the peptide is biologically active. At such a high concentration, it is likely that non-specific binding effects are magnified in relation to specific binding such that the binding equilibrium of the receptor/ligand is skewed. Thus, those peptides showing optimal binding activity candidates.

For example, NT-14 and NT-15 are without effect at any concentration tested, NT-17 is approximately equally active across a broad range of concentrations, while NT-16 and NT-18 are most efficacious at $10^{-5}$M. By taking into account the concentration and the experimental error, it is reasonable to exclude these peptides as not being biologically active.

However, it is noted that D-cycloserine is a partial agonist at the glycine site of the NMDA receptor, and can act as a cognitive enhancer (Thompson, Moskal and Disterhoft, 1992, Nature, 359:638–641). Serine and threonine do share many structural features, such that it may be possible for threonine to have similar enhancing properties as serine. Thus it is possible to predict that replacing the threonine moieties of NT-3 and NT-13 with serine, will result in active peptides.

EXAMPLE 3

Electrophysiological NMDA Specific Activity Assay

Direct electrophysiological measurement of the effects of the peptides of the instant invention on NMDA receptor function is a powerful, unambiguous, and relatively cost and time efficient screening method. Peptides of the instant invention, first selected as favorable via the [$^3$H]MK-801 binding assay, are then subjected to electrophysiological screening.

Methods Electrophysiological recordings are made with two-electrode voltage-clamp techniques, and standard oocyte expression system preparations (see Leonard and Kelso, 1990, Neuron 4:53–60; Kelso et al., 1992, J. Physiology 449:705–718). Oocytes are isolated and injected with mRNA for mouse NMDA receptor subunits: 70 nl of zl ($\zeta$1) RNA is co-injected with an equal volume of e1 ($\epsilon$1) RNA. After incubation for two days, recordings are made while clamping the membrane potential at −80 mV. The standard recording solution contains 95 mM NaCl, 2 mM KCl, 3.8 mM BaCl$_2$, and 5 mM HEPES. Mg$^{2+}$ is omitted because it blocks NMDA currents at some potentials; Ca$^{2+}$ is omitted because it can trigger the oocyte's endogenous Ca$^{2+}$-dependent chloride current. Responses are evoked by the continuous perfusion of 3–5 ml of NMDA containing solutions. The recording chamber has a volume of about 400 ml. In some experiments, 7-chlorokynurenic acid is added to the perfusion solution to demonstrate that the peptides or amino acid compositions tested are able to compete with, and act at the glycine binding site.

Data Analysis/Interpretation

Figure 3A:
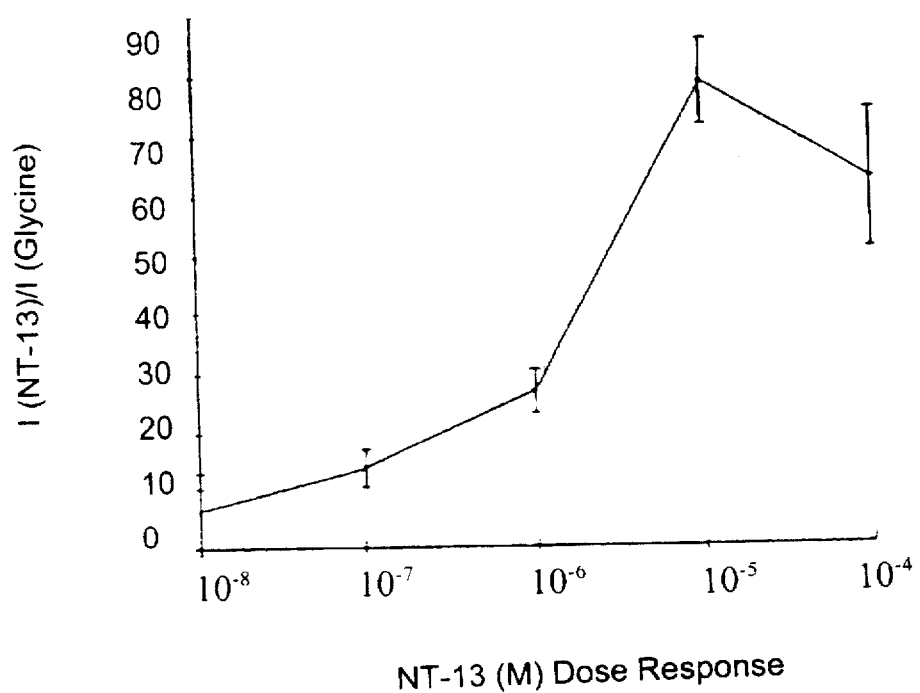
FIG. 3 shows the results of testing peptide NT-13 as a partial agonist in voltage-clamp experiments in an oocyte

FIG. 3A shows that peptide NT-13 has a dose-dependent effect on NMDA currents. Increasing concentrations cause increased currents.

Figure 3B:
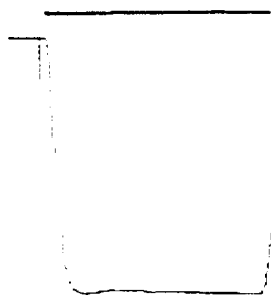
Figure 3B:
Figure 3B:
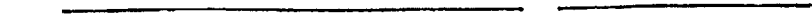

FIG. 3B shows that peptide NT-13 enhances NMDA current, in the absence of glycine. Here, 100 µM NMDA with 10 µM glycine elicited a large current (about 284 nA, downward deflection of trace). In the next phase, 100 µM NMDA with 100 µM peptide NT-13 elicited a significant current of about 40% of the saturated glycine+NMDA response. In this same cell, NMDA alone showed only a negligible response (about 7 nA).

Figure 3C:
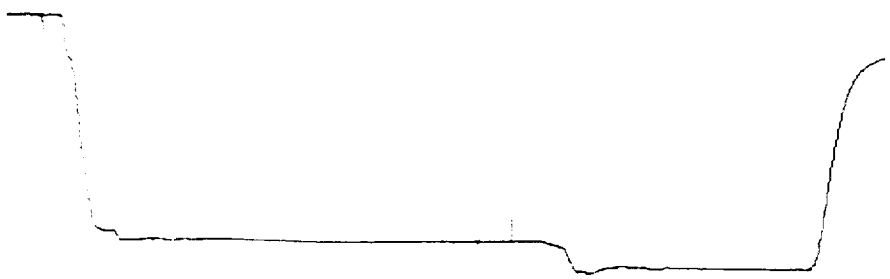

FIG. 3C shows that at high glycine concentrations, added peptide NT-13 reduces NMDA current, here a reduction to about 91% of the control response to NMDA and saturating glycine. This data further supports the conclusion that the peptide competes at the glycine binding site.

Figure 3D:
Figure 3D:

FIG. 3D shows that in the absence of glycine, the effect of peptide NT-13 was blocked by the selective addition of the antagonist 7-chlorokynurenic acid.

EXAMPLE 4

Behavioral NMDA Specific Activity Assay

Morris water maze (MWM)

There are two types of hippocampus (HPC)-dependent associative learning; a temporal-dependent and a spatial-dependent. The Morris water maze (Morris, 1984, J. Neurosci. Meth. 11:47–60; Brandeis et al., 1989, Int. J. Neurosci. 48:29–69) is a well-established paradigm for measuring spatial-dependent learning, and thus complements other behavioral assays such as eyeblink studies which measure temporal learning. Both types of learning are affected by aging and are dependent on NMDA receptor activation (Morris, 1989, J. Neurosci. 9:3040–3057).

Method of Approach

Adult male Sprague-Dawley rats are used in all experiments. A total of 8 to 10 animals per group are used. The number of animals per group was selected upon power function analysis of previous data obtained in similar work. Based upon the outcome of these prior studies, realistic estimates of error variance for biochemical and behavioral endpoints were obtained. Using this information and establishing the value as p<0.05, the sample size was selected which would provide acceptable levels of statistical power. Estimates were based upon suggestions presented in Keppel (Design and Analysis, Prentice Hall, NY, 1973). In all instances, studies were designed to maximize the amount of information derived from a minimum number of animals.

Rats are implanted with stainless steel guide cannulae in both the left and right lateral ventricle of the brain. Behavioral testing begins after the rats have rested for two weeks. Fifteen minutes prior to each days training session in the water maze task, described below, rats are infused with peptide at appropriate concentrations, or with artificial cerebrospinal fluid control vehicle (aCSF). Solutions are infused at a rate of about 1.0 ml/min into the cerebral ventricles (i.c.v.) using a 30 gauge injection cannula connected by PE-10 tubing to a 10 ml Hamilton syringe mounted in a CMA Instruments precision infusion pump. A total of about 3.0 ml is infused into each ventricle. To promote diffusion, the injection cannula is left in place for a period of two minutes following infusion. Acute injection procedures are used so as to maintain a specific treatment-testing interval. A non-injected control group is included to assess the effects of the injection procedure itself on the performance.

Water Maze Task

Fifteen minutes following i.c.v. injection, rats are tested in a Morris water maze task. This task is widely used to assess the behavioral properties and neurobiological substrates of spatial memory in rats. It has become popular since it is a rapidly acquired behavior, and is not motivated by food deprivation. Numerous studies have shown that performance of this task is dependent upon intact hippocampal and septohippocampal cholinergic circuitry. Task performance is disrupted by (i) surgical, or (ii) pharmacological disruption of the HPC or its cholinergic innervation, and by (iii) aging. It is accepted that this task provides a sensitive and useful behavioral assay for the functional intergrity of the septohippocampal pathway and the HPC (Opello et al., 1993, *Physiol. Behav.* 54(6):1227–1233).

The standard MWM task requires rats to learn to swim to a submerged platform in a circular pool containing opaque water. Four equally spaced points around the edge of the pool are designated as start positions, and divide the pool into four equal quadrants. The submerged escape platform is located in one of the four quadrants throughout training. Each training trial consists of placing the rat into the water at one of the four start positions. The rat is allowed to search for the submerged platform for up to 60 seconds, and is allowed to remain on the platform for 30 seconds. The rats are tested for two trials per day, for 15 consecutive days. Different start positions around the pool are presented in a random sequence. Latency to swim to the submerged platform serves as the measure of acquisition. These testing parameters provide a task that is sensitive to both treatment-induced improvements and impairments of spatial memory. A second component of testing involves the introduction of of probe trials after trials 2, 14, 26 and 38. During the probe trials the escape platform is removed and the rat's behavior is videotaped for 30 seconds. The following measures are derived by an automated video tracking system: (i) percent of time spent swimming in the correct quadrant, (ii) average distance from the target during the probe trial, and (iii) swim speed. The use of this sequential probe trial procedure allows the assessment of different components of spatial learning; procedural memory, a form of memory not related to hippocampal functions, and declarative memory, a HPC-dependent process. It is important to evaluate these two forms of cognition since only declarative memory is compromised in aging, Alzheimer's disease, and in the AF64A model (Opello et al., 1993, *Physiol. Behav.* 54(6):1227–1233).

Histological Analysis

Following the completion of the behavioral studies, rats are sacrificed and prepared for histological examination. Analysis is done to determine if repeated injection of peptides produce any signs of excitotoxic damage in the HPC. Blocks of HPC will be drop fixed in a 0.1M phosphate buffer solution containing 10% formalin and 30% sucrose. Coronal sections are cut and stained with cresyl violet. Staining of the pyramidal cell layers in CA3 and CA1 is measured with an image analysis system.

Data Analysis/Interpretation

Overall treatment effects are assessed using either a one or two way analysis of variance (ANOVA), depending on the occurrence of multiple factors or repeated measures, according to a mixed model ANOVA. Appropriate pair-wise comparisons are performed using Fisher's Least Significant Difference (LSD) test. Acceptable statistical significance is $p<0.05$, and all post-hoc tests are two-tailed.

Results

Figure 4A:
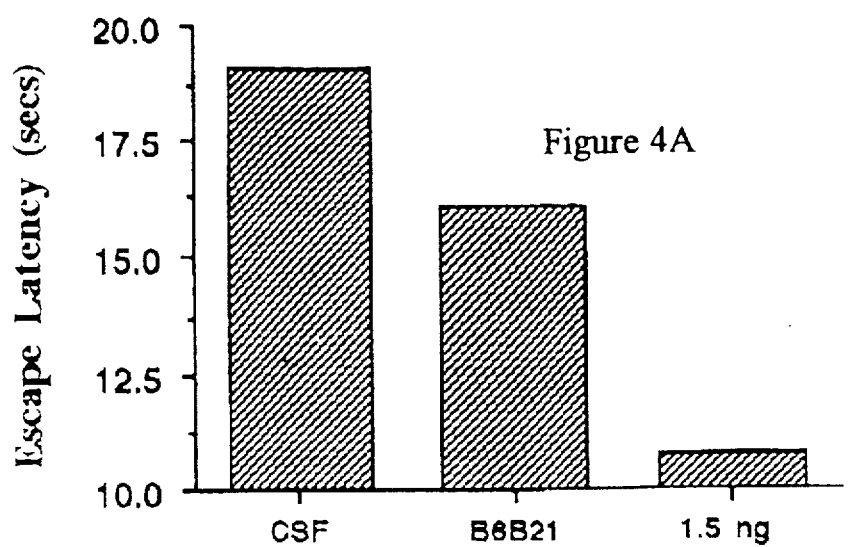
Figure 4B:
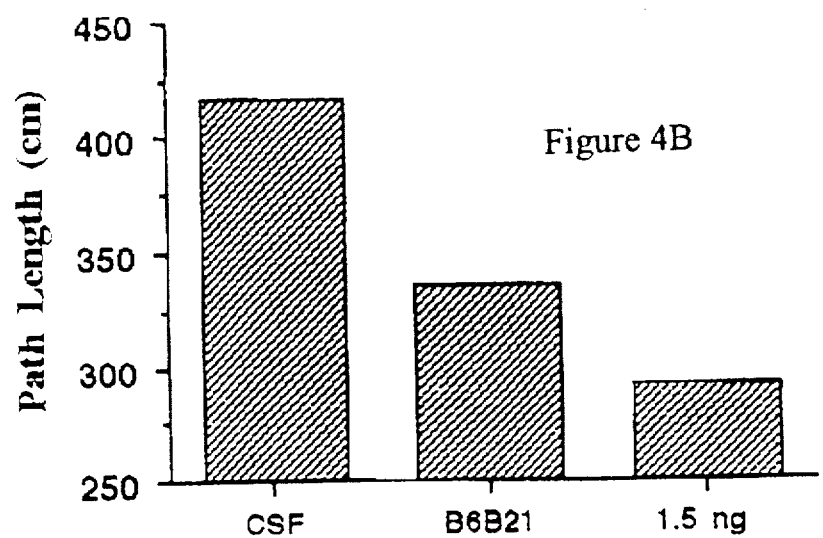
Figure 4C:
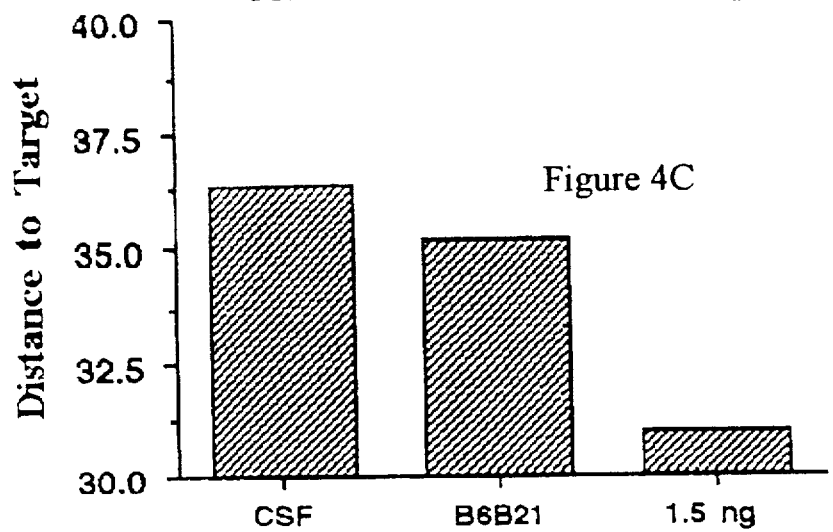

FIG. 4 shows the results of testing peptide NT-13 as a partial agonist in a behavioral NMDA-specific function assay compared with artificial cerebral spinal fluid control (aCSF) and mAb B6B21. The results show that peptide NT-13 produced some cognitive enhancement in the Morris water maze task as measured by shorter latencies to swim to the submerged platform (FIG. 4A), decreased path lengths to the platform (FIG. 4B), and decreased average distance to the target during the probe trial on Day 8 of training (FIG. 4C). The data in FIG. 4A are presented as Escape Latency in seconds for each tested treatment. Here the rats treated with peptide NT-13 showed markedly improved escape latency time (about 10.75 seconds) as compared with CSF control (about 19 seconds), and mAb B6B21 treated animals (about 16.25 seconds). The data in FIG. 4B are presented as Path Length in centimeters for each tested treatment, where rats treated with peptide NT-13 showed decreased path length to target (about 300 cm), as compared to control CSF treated (about 420 cm) and mAb B6B21 treated animals (about 330 cm). The data in FIG. 4C are presented as Distance to Target in centimeters for each tested treatment, where the average distance from the target, once removed during the probe trial, is used as a measure for retention. Here rats treated with peptide NT-13 stayed very close to the location of the removed target, an average distance of about 31 cm, while control CSF and mAb B6B21 treated animals strayed about 36.25 cm and 35 cm, respectively.

These data demonstrate that treatment with the peptide of the instant invention can induce in vivo behavioral effects in mammals, specifically cognitive enhancement as demonstrated by improved performance in the Morris water maze task.

EXAMPLE 5

Behavioral NMDA Specific Activity Assay—Trace Eyeblink

Trace Eyeblink Conditioning

Eyeblink or nictitating membrane conditioning has been adapted as a "model behavioral system" for use in the analysis of neural substrates of learning by several laboratories (Disterhoft et al., 1977, *Brain Res.* 137:127–143; Thompson, 1976, *American Psychologist* 31(3):209–227). Among the advantages of this system are the relative simplicity of the behavioral paradigm, the excellent control procedures available, the fact that associative learning is being analyzed, the ease of conditioned and unconditioned stimulus application and control, the ease of precise behavioral and neurophysiological measurement, and the extensive body of behavioral data which are available for this preparation (Gormezano, 1966, in *Classical Conditioning*, J. B. Sidowski ed., McGraw Hill, New York, pp.385–420; Gormezano et al., 1987, *Classical Conditioning*, Hillsdale, N.J.). The system has been correlated with several pathologies, including memory disorders related to aging (Solomon et al., 1988, *Neurobiol. Aging* 9:535–546), calcium deficiency and aging (Disterhoft et al., 1994, *Annals NY Acad. Sci.* 747:382–406), amnesia (Gabrieli et al., 1995, *Behav. Neurosci.* 109:819–827), and amnesic Korsakoff's patients and recovered alcoholics (McGlinchey-Berroth et al., 1995, *Alcoholism: Clin. and Exp. Res.* 19:1127–1132).

Method of Approach

Female adult albino rabbits, *Oryctolagus cuniculus* were surgically implanted with lateral ventricular guide cannulae bilaterally and fitted with restraining headbolts. Surgery was performed at least one week after arrival, and dosages for anesthesia were calculated according to weight (60 mg/kg ketamine-HCl, 10 mg/kg xylazine).

Approximately 10 days after surgery subjects were given a single, one hour session of habituation to the training environment. Training began after two days of rest. Rabbits were restrained using snug bags with drawstrings at the front and rear and trained in separate sound attenuated chambers. The rabbits were placed in a padded plexiglass stock similar to that described by Gormezano et al. (1966, in *Classical Conditioning*, J. B. Sidowdiki ed., McGraw Hill, New York, pp.385–420) with a bar attached for head restraint. The eyelids were held open with dress hooks and nictitating membrane extension was measured with an infared reflective sensor (Thompson et al., 1994, *J. Neurosci. Meth.*, 54:109–117).

Prior to each training session, rabbit pairs received bilateral infusions of 5 µl of either B6B21 suspended in artificial cerebral spinal fluid (aCSF; 124 mM NaCl, 26 mM NaHCO$_3$, 3 mM KCl, 2.4 mM CaCl$_2$, 1.3 mM MgSO$_4$, 1.24 mM NaH$_2$O$_4$, 10 mM D-glucose; pH 7.4), or of aCSF alone at a rate of 1 µl/min/ventricle. Three concentrations of B6B21 were used; 0.3 µg/µl, 1.0 µg/µl or 3.0 µg/µl. The person conducting the experiment was blind as to the contents of the administered solution. Cannulated rabbits were trained in pairs counterbalanced among the four treatment groups with a maximum of six animals in each group.

Trace nictitating membrane conditioning began immediately after infusion. Training was given for 15 days with 80 trials/day (CS: 6 kHz, 90 dB, 100 msec, 5 msec rise/fall time; UCS: 3.5 psi tone, 150 msec). The trace interval was 500 msec to make the task dependent upon the hippocampus (Moyer et al., 1990, *Behav. Neurosci.* 104(2):243–252). Trials were presented with a variable 30–60 sec intertrial interval and controlled by an IBM PC-compatible computer system (Akase et al., 1994, *J. Neurosci. Method.* 54:119–130; Thompson et al., 1994, *J. Neurosci. Meth.*, 54:109–117).

Data Analysis/Interpretation

Overall treatment effects are assessed using either a one- or two-way analysis of variance (ANOVA), depending on the occurrence of multiple factors or repeated measures, according to a mixed model ANOVA. Appropriate pair-wise comparisons are performed using Fisher's Least Significant Difference (LSD) test. Acceptable statistical significane is p<0.05, and all post-hoc tests are two-tailed.

Results

In order to compare behavioral measures based upon the dosages of antibody B6B21 received, rabbits were grouped according to total amount of B6B21 received each day; a CSF control, 1.5 µg, 3.0–5.0 µg, and 10.0–15.0 µg. The 1.5 µg B6B21 drug group was not included in the statistical analyses because it consisted of only one subject.

Figure 5:
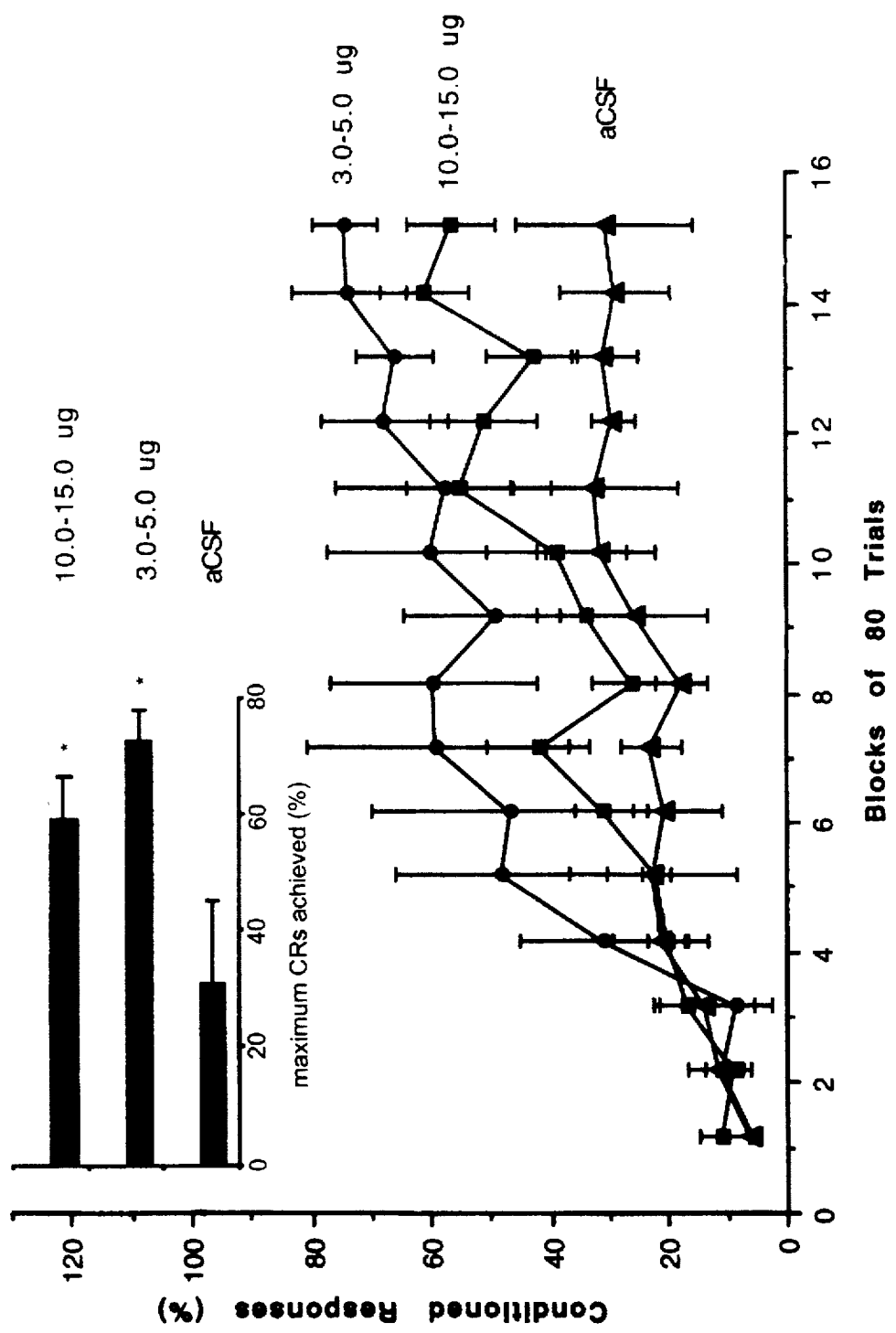
FIG. 5 shows the results of eyeblink conditioning in aging rabbits after treatment with mAb B6B21. Inset shows data for acquisition as maximum CRs achieved.

The final results showed that B6B21 administration enhanced acquisition of the trace conditioned eyeblink response in aging rabbits in a dose dependent manner (FIG. 5). Using an identical trace conditioning protocol, Thompson et al., (1995, *Neurobiol. Aging* 747:382–406) reported that 40% of 36+ month-old rabbits (n=50) reached a criteria of 80% CRs within 25 days of training. The remaining 60% of the rabbits failed to perform at a level>30%, and were referred to as "severely impaired." The aCSF controls (n=2) in the present study performed in a similar fashion to Thompson's "severely impaired" animals, as did the one animal receiving 1.5 µg B6B21 (Low Dose; n=1, data not shown). None of the rabbits in the present study, who received 10.0–15.0 µg B6B21 (High Dose; n=3) reached 80% CRs within 15 days. However, rabbits receiving 3.0–5.0 µg B6B21 (Intermediate Dose; n=4) began to show greater acquisition on Day 5 as compared to all other groups, and showed greater acquisition than controls as measured by the maximum CRs achieved (Student t-test: t(4)=3.34, p≦0.05, see FIG. 5 inset).

The average percentage of CRs during the final week of training was generated for each group to measure learning. A one-way ANOVA between control and experimental groups indicated significant differences between group means (F(3,12)=3.9, p≦0.05, p=0.037). A Fisher's PLST post-hoc T-test comparison between control and 3.0–5.0 µg groups showed enhanced learning (P(T≦t) one-tail=0.03, p≦0.05), whereas the higher dosage group did not show a significant difference in acquisition in the same post-hoc t-test (P(T≦t) one-tail=0.09).

While the overall number of animals used for statistical analyses is small, these results clearly demonstrate that mAb B6B21 significantly enhances the acquisition of trace eyeblink conditioning in aging rabbits in a dose-dependent fashion. These results show that there is reasonably expected success in developing biologically active B6B21 peptide mimetics.

EXAMPLE 6

Hypothetical Example

Behavioral NMDA Specific Activity Assay—Trace Eyeblink in Rats

Method of Approach

The F1 hybrid of Fisher 344xBrown Norway rats are used because of minimal age-related pathology (Bronson, 1990, in *Genetic Effects on Aging II*, Harrison, D. E. ed., Telford Press, Caldwell, N.J.), and age-related impairments in eyeblink conditioning (Weiss and Thompson, 1992, *Neurobiol. Aging* 13:319–323). Nine month old, virgin male rats are used in the experiments.

Rats are anesthetized with an intraperitoneal injection of sodium pentobarbital (65 mg/kg body weight). The top of the head is shaved and cleaned with alcohol and betadine. A stereotaxic device with a gas anesthesia adapter and atraumatic ear bars (to protect the ear drums) are used. Once the animal is carefully secured, a midline incision is made on the scalp. The skin of the pereosteum is retracted and the skull cleaned and dried. A hole is drilled through the skull approximately 0.8 mm behind the bregma, and 1.3 mm to the right and left of the midline (level head coordinates). The dura is then pierced, and a 25-gauge cannula is lowered into each hole to a depth of 4.0 mm below the cortical surface (Tonkiss and Rawlins, 1991, *Exp. Brain Res.* 85:349–358). These guide cannulae are then cemented to the skull with dental acrylic. A strip connector is cemented to the skull anterior to the cannula. The connector contains a ground wire, two wires (teflon™ coated stainless steel) which are implanted subdermally within the upper eyelid to measure EMG activity, and two wires which are implanted to deliver a periorbital shock. Subjects are given one week of recovery before habituation.

Fifteen minutes prior to each days training session, described below, rats are infused with peptide at appropriate concentrations, or with artificial cerebrospinal fluid control vehicle (aCSF). Solutions are infused at a rate of about 1.0 ml/min into the cerebral ventricles (i.c.v.) using a 30 gauge injection cannula connected by PE-10 tubing to a 10 ml Hamilton syringe mounted in a CMA Instruments precision infusion pump. A total of about 3.0 ml is infused into each ventricle. To promote diffusion, the injection cannula is left in place for a period of two minutes following infusion. Acute injection procedures are used so as to maintain a specific treatment-testing interval. A non-injected control group is included to assess the effects of the injection procedure itself on the performance.

Rats are placed in a small cage in a sound attenuated chamber that has a speaker and ventilation fan. A cable is then connected between the experimental equipment and the strip connector implanted on the head. The conditioning stimuli is controlled by software running on a PC compatible computer and electronic modules from Coulbourn Instruments (Akase et al., 1994, *J. Neurosci. Meth.* 54:119–130). The EMG activity is amplified, filtered, and full wave rectified with a time constant of 45 ms (Skelton, 1988, *Behav. Neurosci.* 102:586–590). The signal is sent to a computer for data collection and analysis (Thompson et al., 1994, *J. Neurosci. Meth.* 54:109–117).

Eyeblink conditioning is done using modified procedures as reported by Weiss and Thompson (1992, *Neurobiol. Aging* 13:319–323). The rats are habituated to the conditioning apparatus for one 45 minute session prior to training sessions. Animals are trained daily in pairs for 15 days with either trace 500 paradigm or the unpaired control paradigm for psuedoconditioning. Rats are trace eyeblink conditioned using a tone conditioning stimulus (CS, 100 ms, 1 KHz, 85 dB, 5 ms rise/fall time) and a periorbital shock unconditioned stimulus (US, 150 ms, 2 mA AC). The stimulus free trace period is 500 ms to make the task dependent upon the hippocampus (Moyer et al., 1990, *Behav. Neurosci.* 104(2) :243–252). Conditioned rats receive 80 trials with paired tones and shocks at a random interval (ITI) of 30–60 seconds. Control rats receive 160 trials with either a tone alone, or a shock alone, at a random ITI of 15–30 seconds. After the conditioning sessions each rat undergoes five days of extinction training consisting of 80 sessions of tone alone trials with a 30–60 second ITI.

Histological Analysis

Following the completion of the behavioral studies, rats are sacrificed and prepared for histological examination. Analysis is done to determine if repeated injections of peptide produce any signs of excitotoxic damage in the HPC. Blocks of HPC will be drop fixed in a 0.1M phosphate buffer solution containing 10% formalin and 30% sucrose. Coronal sections are cut and stained with cresyl violet. Staining of the pyramidal cell layers in CA3 and CA1 is measured with an image analysis system.

Data Analysis/Interpretation

The data is analyzed with ANOVAs (one- or two-way analysis of variance) of group (conditioned vs. controls)× dose (ACSF and 3 doses). The repeated measures will also be analyzed with ANOVAs. The ANOVA for acquisition will include 15 levels in the ANOVA. The ANOVA for extinction will include 5 levels. This factorial design yields 8 groups of animals with about 10 animals per group used for reliable statistical analysis.

EXAMPLE 7

Future Autoradiography Studies

The peptides of the instant invention allow for the exquisite study of the brain tissue distribution of the biologically active peptide and/or receptors.

Method of Study

By adapting the autoradiographic methods of Bekenstein et al. (1990, *Brain Res.* 126:397–425) to the peptides of the instant invention, we will be able to examine the regional binding specificity throughout the hippocampal region of the brain, as well as other tissues. In the initial studies, optimized binding conditions will be developed in terms of preincubations and washings, methods of drying, equilibrium of time course, saturation, and pharmocology of the binding site at 23° C. Naive rats will be sacrificed, the brains rapidly removed, embedded in OCT, and frozen in 2-methyl butane at −20° C. prior to sectioning. Ten μm coronal sections will be cut on a cryostat and thaw-mounted on poly-D-lysine coated coverslips. Serial sectioning will permit assessment of binding gradients along the entire septo-temporal and dorsal-ventral extent of the hippocampus. In the event that gradients in binding within (rather than across) specific hippocampal subfields or cell populations are found, we will take particular care to perform Scatchard analyses only within areas free from such gradients. Adjacent sections will be used for Nissel stained histological examination and for determination of nonspecific binding. Individual sections will be preincubated in several repeated volumes of 20 mM HEPES buffer (pH. 7.4) to reduce concentrations of endogenous or exogenous ligands. Tissue will be incubated with an optimized concentration of [$^3$H]-peptide of the instant invention, in 20 mM HEPES buffer for varying periods of time, to determine equilibrium binding for saturation studies. For saturation experiments, brain sections will be incubated with varying concentrations of [$^3$H]-peptide of the instant invention, in 20 mM HEPES buffer. Nonspecific binding will be determined with the addition of excess cold peptide.

Analysis/Interpretation

Tissue sections will be apposed to [$^3$H]-Ultrofilm (Amersham) and coexposed with methacrylate embedded tritium standards as needed for linear exposure of the film. A BioRad Phosphorimage Analyser will be used for these studies. Quantitative densitometric analysis will be performed on a Macintosh IIfx workstation with an 8-bit grey scale scanner, and public domain image analysis software (Image™ v. 1.29) developed at NIMH.

It will be understood that the specification and examples above are illustrative, and not meant by way of limitation. One of ordinary skill in the art will be able to understand and determine from the teaching of the instant invention that other specific embodiments may be within the spirit and scope of the invention.

We claim:

1. A polypetide or amino acid composition consisting of at least one isolated polypeptide having amino acid composition consisting of consisting of Gln-Gln-His-Tyr-Ser-Thr-Pro-Pro-Thr (Seq ID No:3)

Val-Try-Try-Ser-Gln-Gln-His-Tyr-Ser-Thr-Pro-Pro-Thr (Seq ID No:4)

Glu-Asp-Leu-Ala-Val-Tyr-Tyr-Ser-Gln-Gln-His-Tyr-Ser-Thr-Pro-Pro-Thr (Seq Id No:5)

Gln-Gln-His-Tyr-Ser-Thr-Pro-Pro-Thr-Phe-Gly-Gly-Gly-Thr-Lys-Leu-Glu (Seq ID No:9)

Cys-Gln-Gln-His-Tyr-Ser-Thr-Pro-Pro-Thr-Cys (Seq ID No:10)

Ser-Gln-Gln-His-Tyr-Ser-Thr-Pro-Pro-Thr-Ser (Seq ID No:11)

Gln-Gln-His-Tyr-Ser (Seq ID No:12)

3Thr-Pro-Pro-Thr (Seq ID No:13).

2. A composition of claim 1 wherein said polypeptide is cyclized by creating a suitable linkage between the carboxy terminal and amino terminal amino acids of said polypeptide.

3. A pharmaceutical composition comprising an effective N-methyl-D-aspartate (NMDA) receptor binding amount of a polypeptide or amino acid composition of claim 1, in a suitable carrier.

4. A composition of claim 3 wherein said polypeptide is cyclized by creating a suitable linkage between the carboxy terminal and amino terminal amino acids of said polypeptide.

5. A pharmaceutical composition comprising an effective N-methyl-D-aspartate (NMDA) receptor binding amount of a polypeptide or amino acid composition of claim 1, wherein said polypeptide or amino acid component of said composition is at a concentration from about $10^{-5}M$ to the limit of solubility of the composition in a suitable pharmaceutical carrier.

6. A composition of claim 5 wherein said polypeptide is cyclized by creating a suitable linkage between the carboxy terminal and amino terminal amino acids of said polypeptide.

* * * * *

UNITED STATES PATENT AND TRADEMARK OFFICE
CERTIFICATE OF CORRECTION

PATENT NO. : 5,763,393
DATED : June 9, 1998
INVENTOR(S) : Moskal et al.

It is certified that error appears in the above-identified patent and that said Letters Patent is hereby corrected as shown below:

At column 23, line 42-43:

The phrase

"having amino acid composition consisting of consisting of"

should correctly read

- -having an amino acid sequence selected from the group consisting of- -

At column 23, line 57:

The word "3Thr" should read - -Thr- -

Signed and Sealed this

Eighth Day of September, 1998

*Attest:*

BRUCE LEHMAN

*Attesting Officer*   Commissioner of Patents and Trademarks

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
        ( A ) LENGTH: 11 amino acids
        ( B ) TYPE: amino acid

```
            ( C ) STRANDEDNESS: single
            ( D ) TOPOLOGY: Not Relevant ( i i ) MOLECULE TYPE: peptide ( i x ) FEATURE:
            ( A ) NAME/KEY: Peptide
            ( B ) LOCATION: 1
            ( D ) OTHER INFORMATION: /note= "NT-1"

( x i ) SEQUENCE DESCRIPTION: SEQ ID NO:1:

Lys  Ala  Ser  Gln  Asp  Val  Ser  Thr  Thr  Val  Ala
    1              5                        10
```

( 2 ) INFORMATION FOR SEQ ID NO:2:

```
    ( i ) SEQUENCE CHARACTERISTICS:
            ( A ) LENGTH: 7 amino acids
            ( B ) TYPE: amino acid
            ( C ) STRANDEDNESS: single
            ( D ) TOPOLOGY: Not Relevant ( i i ) MOLECULE TYPE: peptide ( i x ) FEATURE:
            ( A ) NAME/KEY: Peptide
            ( B ) LOCATION: 1
            ( D ) OTHER INFORMATION: /note= "NT-2"

( x i ) SEQUENCE DESCRIPTION: SEQ ID NO:2:

Ser  Ala  Ser  Tyr  Arg  Tyr  Thr
    1              5
```

( 2 ) INFORMATION FOR SEQ ID NO:3:

```
    ( i ) SEQUENCE CHARACTERISTICS:
            ( A ) LENGTH: 9 amino acids
            ( B ) TYPE: amino acid
            ( C ) STRANDEDNESS: single
            ( D ) TOPOLOGY: Not Relevant ( i i ) MOLECULE TYPE: peptide ( i x ) FEATURE:
            ( A ) NAME/KEY: Peptide
            ( B ) LOCATION: 1
            ( D ) OTHER INFORMATION: /note= "NT3"

( x i ) SEQUENCE DESCRIPTION: SEQ ID NO:3:

Gln  Gln  His  Tyr  Ser  Thr  Pro  Pro  Thr
    1              5
```

( 2 ) INFORMATION FOR SEQ ID NO:4:

```
    ( i ) SEQUENCE CHARACTERISTICS:
            ( A ) LENGTH: 13 amino acids
            ( B ) TYPE: amino acid
            ( C ) STRANDEDNESS: single
            ( D ) TOPOLOGY: Not Relevant ( i i ) MOLECULE TYPE: peptide ( i x ) FEATURE:
            ( A ) NAME/KEY: Peptide
            ( B ) LOCATION: 1
            ( D ) OTHER INFORMATION: /note= "NT-4"

( x i ) SEQUENCE DESCRIPTION: SEQ ID NO:4:

Val  Tyr  Tyr  Ser  Gln  Gln  His  Tyr  Ser  Thr  Pro  Pro  Thr
    1              5                        10
```

( 2 ) INFORMATION FOR SEQ ID NO:5:

(i) SEQUENCE CHARACTERISTICS:
  (A) LENGTH: 17 amino acids
  (B) TYPE: amino acid
  (C) STRANDEDNESS: single
  (D) TOPOLOGY: Not Relevant (ii) MOLECULE TYPE: peptide (ix) FEATURE:
  (A) NAME/KEY: Peptide
  (B) LOCATION: 1
  (D) OTHER INFORMATION: /note= "NT-5"

(xi) SEQUENCE DESCRIPTION: SEQ ID NO:5:

Gly Asp Leu Ala Val Tyr Tyr Ser Gln Gln His Tyr Ser Thr Pro Pro
1               5                   10                  15

Thr (2) INFORMATION FOR SEQ ID NO:6:

(i) SEQUENCE CHARACTERISTICS:
    (A) LENGTH: 22 amino acids
    (B) TYPE: amino acid
    (C) STRANDEDNESS: single
    (D) TOPOLOGY: Not Relevant (ii) MOLECULE TYPE: peptide (ix) FEATURE:
    (A) NAME/KEY: Peptide
    (B) LOCATION: 1
    (D) OTHER INFORMATION: /note= "NT-6"

(xi) SEQUENCE DESCRIPTION: SEQ ID NO:6:

Ser Val Gln Ala Glu Leu Asp Leu Ala Val Tyr Tyr Ser Gln Gln His
1               5                   10                  15

Tyr Ser Thr Pro Pro Thr
                20

(2) INFORMATION FOR SEQ ID NO:7:

(i) SEQUENCE CHARACTERISTICS:
    (A) LENGTH: 26 amino acids
    (B) TYPE: amino acid
    (C) STRANDEDNESS: single
    (D) TOPOLOGY: Not Relevant (ii) MOLECULE TYPE: peptide (ix) FEATURE:
    (A) NAME/KEY: Peptide
    (B) LOCATION: 1
    (D) OTHER INFORMATION: /note= "NT-7"

(xi) SEQUENCE DESCRIPTION: SEQ ID NO:7:

Phe Thr Ile Ser Ser Val Gln Ala Glu Leu Asp Leu Ala Val Tyr Tyr
1               5                   10                  15

Ser Gln Gln His Tyr Ser Thr Pro Pro Thr
                20                  25

(2) INFORMATION FOR SEQ ID NO:8:

(i) SEQUENCE CHARACTERISTICS:
    (A) LENGTH: 13 amino acids
    (B) TYPE: amino acid
    (C) STRANDEDNESS: single
    (D) TOPOLOGY: Not Relevant (ii) MOLECULE TYPE: peptide ( i x ) FEATURE:
    ( A ) NAME/KEY: Peptide
    ( B ) LOCATION: 1
    ( D ) OTHER INFORMATION: /note= "NT-8"

( x i ) SEQUENCE DESCRIPTION: SEQ ID NO:8:

```
Gln Gln His Tyr Ser Thr Pro Pro Thr Phe Gly Gly Gly
1               5                   10
```

( 2 ) INFORMATION FOR SEQ ID NO:9:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: Not Relevant ( i i ) MOLECULE TYPE: peptide ( i x ) FEATURE:
        ( A ) NAME/KEY: Peptide
        ( B ) LOCATION: 1
        ( D ) OTHER INFORMATION: /note= "NT-9"

( x i ) SEQUENCE DESCRIPTION: SEQ ID NO:9:

```
Gln Gln His Tyr Ser Thr Pro Pro Thr Phe Gly Gly Gly Thr Lys Leu
1               5                   10                  15

Glu
```

( 2 ) INFORMATION FOR SEQ ID NO:10:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: Not Relevant ( i i ) MOLECULE TYPE: peptide ( i x ) FEATURE:
        ( A ) NAME/KEY: Peptide
        ( B ) LOCATION: 1
        ( D ) OTHER INFORMATION: /note= "NT-10"

( i x ) FEATURE:
        ( A ) NAME/KEY: Disulfide-bond
        ( B ) LOCATION: 1..11

( x i ) SEQUENCE DESCRIPTION: SEQ ID NO:10:

```
Cys Gln Gln His Tyr Ser Thr Pro Pro Thr Cys
1               5                   10
```

( 2 ) INFORMATION FOR SEQ ID NO:11:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: Not Relevant ( i i ) MOLECULE TYPE: peptide ( i x ) FEATURE:
        ( A ) NAME/KEY: Peptide
        ( B ) LOCATION: 1
        ( D ) OTHER INFORMATION: /note= "NT-11"

( x i ) SEQUENCE DESCRIPTION: SEQ ID NO:11:

```
Ser Gln Gln His Tyr Ser Thr Pro Pro Thr Ser
1               5                   10
```

( 2 ) INFORMATION FOR SEQ ID NO:12:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: Not Relevant ( i i ) MOLECULE TYPE: peptide ( i x ) FEATURE:
        ( A ) NAME/KEY: Peptide
        ( B ) LOCATION: 1
        ( D ) OTHER INFORMATION: /note= "NT-12"

( x i ) SEQUENCE DESCRIPTION: SEQ ID NO:12:

Gln  Gln  His  Tyr  Ser
    1                       5

( 2 ) INFORMATION FOR SEQ ID NO:13:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: Not Relevant ( i i ) MOLECULE TYPE: peptide ( i x ) FEATURE:
        ( A ) NAME/KEY: Peptide
        ( B ) LOCATION: 1
        ( D ) OTHER INFORMATION: /note= "NT-13"

( x i ) SEQUENCE DESCRIPTION: SEQ ID NO:13:

Thr  Pro  Pro  Thr
    1

( 2 ) INFORMATION FOR SEQ ID NO:14:

( i ) SEQUENCE CHARACTERISTICS:
        ( A ) LENGTH: 3 amino acids
        ( B ) TYPE: amino acid
        ( C ) STRANDEDNESS: single
        ( D ) TOPOLOGY: Not Relevant ( i i ) MOLECULE TYPE: peptide ( i x ) FEATURE:
        ( A ) NAME/KEY: Peptide
        ( B ) LOCATION: 1
        ( D ) OTHER INFORMATION: /note= "NT-14"

( x i ) SEQUENCE DESCRIPTION: SEQ ID NO:14:

Thr  Pro  Pro
    1

( 2 ) INFORMATION FOR SEQ ID NO:15:

( i ) SEQUENCE CHARACTERISTICS:
        ( A ) LENGTH: 3 amino acids
        ( B ) TYPE: amino acid
        ( C ) STRANDEDNESS: single
        ( D ) TOPOLOGY: Not Relevant ( i i ) MOLECULE TYPE: peptide ( i x ) FEATURE:
        ( A ) NAME/KEY: Peptide
        ( B ) LOCATION: 1
        ( D ) OTHER INFORMATION: /note= "NT-15"

( x i ) SEQUENCE DESCRIPTION: SEQ ID NO:15:

```
   Pro Pro Thr
   1
```

( 2 ) INFORMATION FOR SEQ ID NO:16:

( i ) SEQUENCE CHARACTERISTICS:
        ( A ) LENGTH: 2 amino acids
        ( B ) TYPE: amino acid
        ( C ) STRANDEDNESS: single
        ( D ) TOPOLOGY: Not Relevant ( i i ) MOLECULE TYPE: peptide ( i x ) FEATURE:
        ( A ) NAME/KEY: Peptide
        ( B ) LOCATION: 1
        ( D ) OTHER INFORMATION: /note= "NT-16"

( x i ) SEQUENCE DESCRIPTION: SEQ ID NO:16:

```
   Pro Pro
   1
```

( 2 ) INFORMATION FOR SEQ ID NO:17:

( i ) SEQUENCE CHARACTERISTICS:
        ( A ) LENGTH: 3 amino acids
        ( B ) TYPE: amino acid
        ( C ) STRANDEDNESS: single
        ( D ) TOPOLOGY: Not Relevant ( i i ) MOLECULE TYPE: peptide ( i x ) FEATURE:
        ( A ) NAME/KEY: Peptide
        ( B ) LOCATION: 1
        ( D ) OTHER INFORMATION: /note= "NT-17"

( x i ) SEQUENCE DESCRIPTION: SEQ ID NO:17:

```
   Thr Pro Thr
   1
```